United States Patent [19]
Fernwood et al.

[11] Patent Number: 4,941,298
[45] Date of Patent: Jul. 17, 1990

[54] REAR RESERVOIR MICRO SANDBLASTER

[76] Inventors: Mark Fernwood, 1341 Camino Tassajara; Thomas S. Blake, 881 Danville Blvd., both of Danville, Calif. 94526

[21] Appl. No.: 250,775

[22] Filed: Sep. 28, 1988

[51] Int. Cl.$^5$ .............................. B24C 7/00; B24C 5/02
[52] U.S. Cl. ........................................ 51/438; 51/427; 51/436; 51/439; 433/88; 433/100
[58] Field of Search .................. 51/427, 436, 438, 439; 433/85, 88, 100

[56] References Cited

U.S. PATENT DOCUMENTS

| | | | |
|---|---|---|---|
| 2,133,149 | 10/1938 | Poncelet | 51/427 |
| 2,577,465 | 12/1951 | Jones | 51/427 |
| 2,641,087 | 6/1953 | Greiser | 51/438 |
| 2,696,669 | 12/1954 | Ikse | 433/85 |
| 2,744,361 | 5/1956 | Larson et al. | 51/427 |
| 3,164,153 | 1/1965 | Zorzi | 433/88 |
| 4,369,607 | 1/1983 | Bruggeman et al. | 51/436 |

Primary Examiner—Frederick R. Schmidt
Assistant Examiner—Jack W. Lavinder

[57] ABSTRACT

Disclosed herein is an apparatus for abrading, etching, polishing and cleaning metallic or non-metallic surfaces that operates through mechanical sandblasting principles. The present invention is embodied in an apparatus for abrading, etching or polishing a surface with a jet stream containing a mixture of solid particles and a gaseous medium. The apparatus comprises a hollow tubular handle with a nozzle at one end for dispensing the mixture of a solid material and a gaseous medium, and a compressed air and pulverulent material receiving member at the other end of the handle. The nozzle section of the apparatus contains a mixing chamber where a vacuum is created by the flowing pressurized gaseous medium, the pressure gradient results in aspiration of the solid material which mixes with and becomes entrained in the gaseous medium flow and passes through the nozzle tip. The pulverulent material is contained in a small rear reservoir secured to a pick-up apparatus which is meshed with a supply receiving member and is located at the opposite end of the apparatus from the nozzle tip.

7 Claims, 3 Drawing Sheets

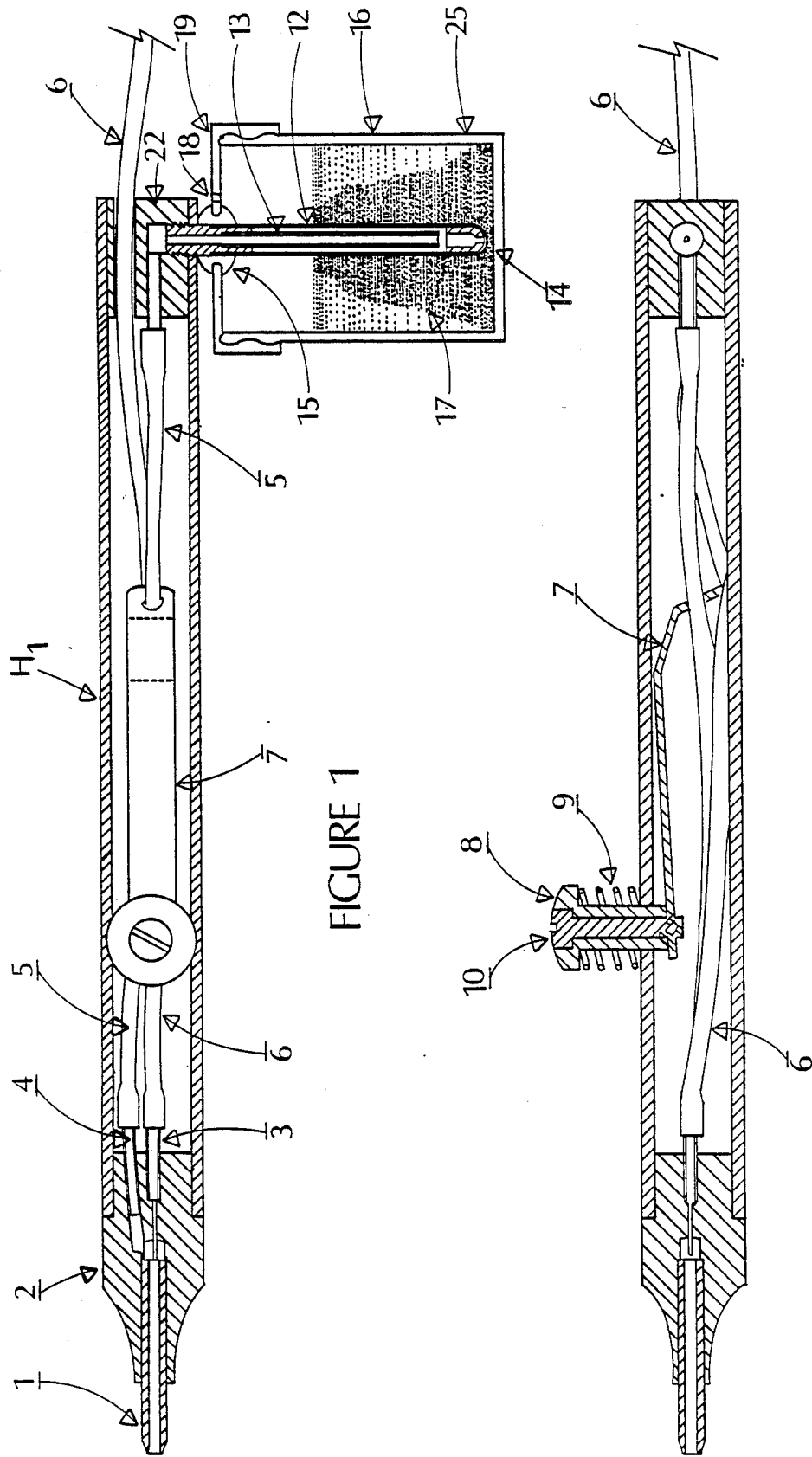

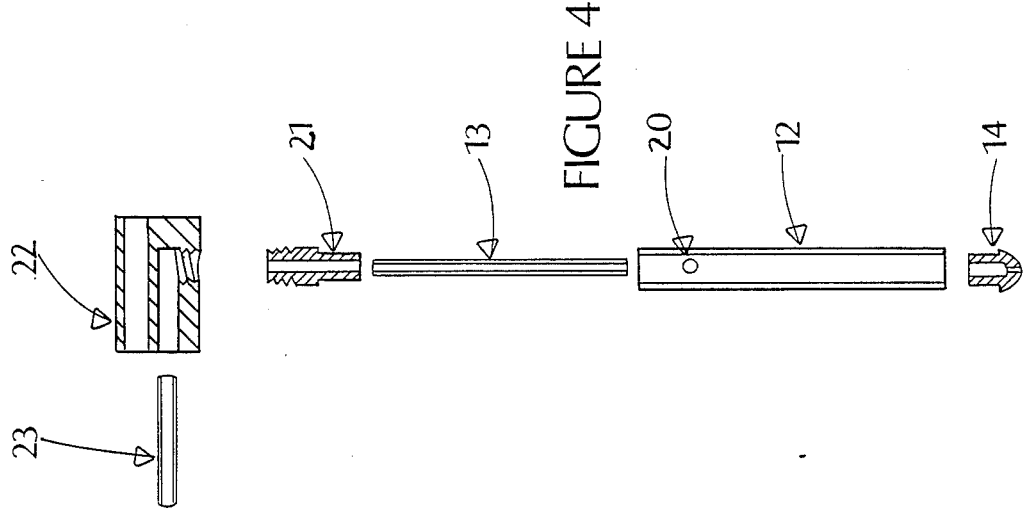
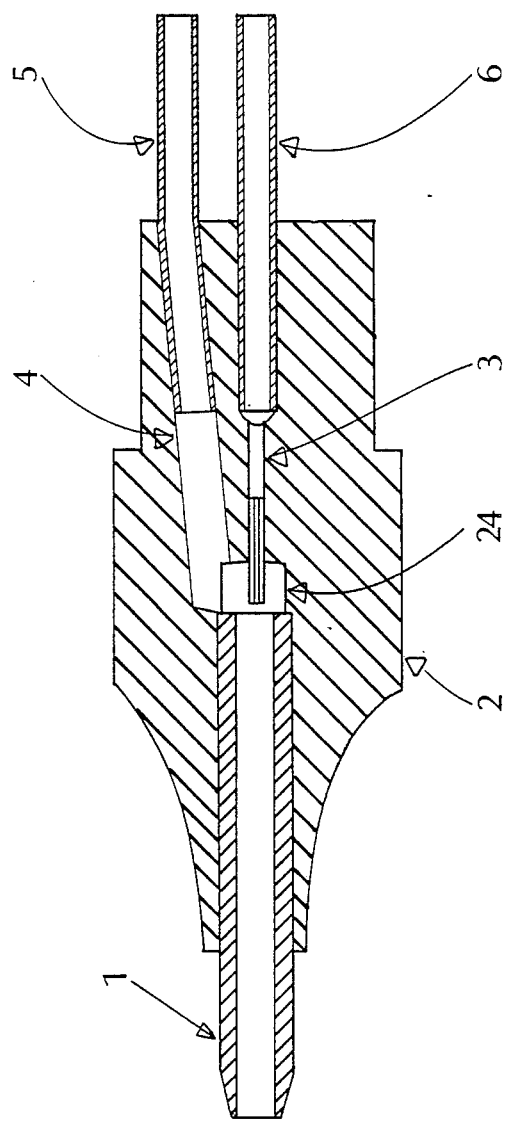

REAR RESERVOIR MICRO SANDBLASTER

BACKGROUND OF THE INVENTION

The present invention relates in general to abrading, polishing and erasing tools designed for delivering or blasting a pulverulent, granular or other finely divided solid material entrained in a air stream against a surface that is to be abraded, polished, or erased. The dental industry and other fields, often require a small reliable sandblaster that is hand operated and has a slim nozzle and handpiece assembly. The slim nozzle and handpiece assembly is especially important so that sandblasting may be done in a confined opening. In the dental industry it is necessary to sandblast in the confinement of a patients mouth in order to prepare tooth structures and inplace crowns for a variety of repair and cementing procedures. It is also highly desirable for the sandblaster to be self-contained in order that separate sandblaster components and reservoirs are not needed as it is cumbersome in a dental operatory.

Conventional devices for abrading, polishing and erasing surfaces have a nozzle which is manipulated by hand and an orifice operating to discharge a jet or stream containing a mixture of small solid particles and compressed air. Conventional apparatus further comprise a stationary source of compressed air and pulverulent material. Instruments of these type are shown in the U.S. Patent issued to Paasche, U.S. Pat. No. 2,441,441, showing an erasing tool; also shown in the U.S. Patent to Kurowski, U.S. Pat. No. 4,090,334 is an erasing tool with a remote pulverulent supply reservoir. The Caron U.S. Pat. No. 3,163,963 shows a blaster device wherein the abrasive material is contained in a canister mounted on the blaster handle.

A drawback of the above outlined apparatus is that the source of pulverulent material is separate from the apparatus resulting in inconvenient operation. Other existing devices have a movable supply of pulverulent material but the location of the supply near the nozzle tip prevents the user from working within a confined space. A drawback of other existing apparatus is their need for a pressurized air supply within the pulverulent material supply canister; to avoid moisture build up these pressurized systems require a dehydrated source of compressed air. Other devices use a mechanical valve to control the pulverulent material flow, this however can result in excessive clogging if moisture enters the system; additionally cleaning of a mechanical valve system is time consuming requiring disassembly of the apparatus. Other apparatus that use a gravity feed system tend to provide an unreliable supply of abrading material and require constant adjustments to the supply valve. Some of the newer inventions have attempted to overcome drawbacks of earlier designs but have however resulted in costly complicated designs.

OBJECTS AND SUMMARY OF THE INVENTION

An object of the present device is to provide a tool that is capable of hand operation within small enclosed spaces, such as the human mouth.

A further object of the invention is to provide a novel and improved apparatus which can be used to abrade, etch, or polish a surface and which is simpler, more compact and less expensive than heretofore known apparatus.

Another object of the invention is to provide the improved apparatus with novel and improved means for confining the supply of pulverulent solid material and means for quickly changing the type of solid material to be used.

A further object of the invention is to provide an apparatus which is less likely to be clogged than conventional apparatus.

Another object of the invention is to provide an apparatus which can supply an unchanging mixture of solid particles and a gaseous carrier medium for any desired interval of time.

An additional object of the invention is to provide the apparatus with a novel and improved handle and to construct and assemble the apparatus in such a way that it can receive a pressurized gaseous medium from sources which are normally available in a dentist's office, in a dental laboratory, in a similar institution or in a applicable industry setting.

A further object of the invention is to provide the improved apparatus with novel and improved means for admitting solid particles and the gaseous carrier medium into the vortex chamber.

Another object of the invention is to provide the improved apparatus with novel and improved means for rapid cleaning of any solid material blockages within the apparatus.

Another object of the invention is to provide the improved apparatus with novel, improved and simplified means for controlling the compressed air flow.

The present invention is embodied in an apparatus for abrading, etching or polishing a surface with a jet stream containing a mixture of solid particles and a gaseous medium. The apparatus comprises a hollow tubular handle with a nozzle at one end for dispensing the mixture of a solid material and a gaseous medium, and a compressed air and pulverulent material receiving member at the other end of the handle. The nozzle section of the apparatus contains a mixing chamber where a vacuum is created by the flowing pressurized gaseous medium, the pressure gradient results in aspiration of the solid material which mixes with and becomes entrained in the gaseous medium flow and passes through the nozzle tip.

The pulverulent material is contained in a small rear reservoir secured to a pick-up apparatus which is meshed with a supply receiving member and is located at the opposite end of the apparatus from the nozzle tip.

The solid material supply line can be provided with simplified means for removing any clogs by simply placing an object securely over the nozzle tip during operation, the resulting action will force air back through the solid material supply and quickly remove all clogs.

The nozzle tip can be located in a direction parallel to the apparatus housing or can be directed at a contra-angle.

The apparatus can operate in a stand-by mode with a pinch lever which inhibits the compressed air flow by compressing the air supply tube. Alternatively, the apparatus can be activated by releasing a pinch lever which allows the supply tube to return to original shape and ends the blockage of the air supply.

The apparatus preferably comprises a solid material reservoir that can quickly be changed by sliding the supply reservoir on or off a pick-up stem.

The present invention will be discussed further in the detailed description which accompanies the referenced drawings. The novel attributes of the present invention are set forth specifically in the succeeding claims.

BRIEF DESCRIPTION OF THE DRAWING

The invention is described in greater detail in the text that follows, with the aid of the accompanying drawings, and in which:

FIG. 1 shows a side view of the abrading apparatus;

FIG. 2 shows a bottom view of the abrading apparatus with detail of the flow control pinch valve shown in detail and the pulverulent supply bottle removed;

FIG. 3 shows in detail the pick-up tube apparatus in an exploded drawing;

FIG. 4 shows in detail the nozzle and nozzle body identified in FIG. 1.

DESCRIPTION OF THE PREFERRED EMBODIMENT

Figure 5:
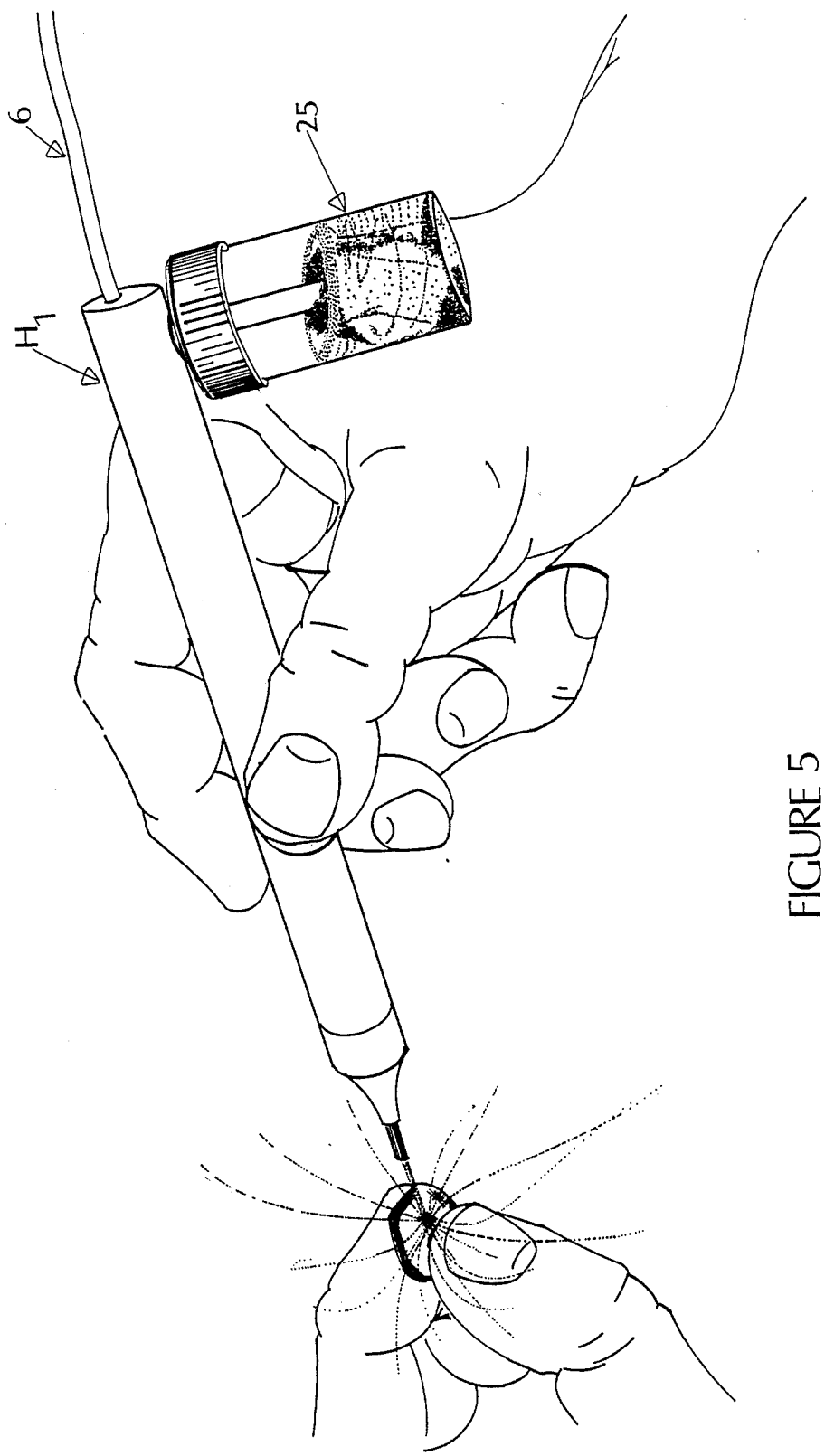
FIG. 5 shows a perspective drawing of the apparatus in a typical use.

Referring first to FIG. 1, there is shown an apparatus for abrading and polishing the surface of a material. The apparatus comprises a hollow elongated housing H1 which constitutes a handle and includes a tubular central section 11, a nozzle 1 at one end of the housing, an air and pulverulent material receiving member mainfold 22 at the other end of the housing and a pinch lever 7 to control the operation of the apparatus. The receiving member has internal threads which can mesh with a pick-up stem 12 serving to connect the housing with the supply of pulverulent material 17; said receiving member 22 also having a hollowed passage to receive an external supply of compressed air.

Referring again to FIG. 1 and additionally to FIG. 2 a pinch lever 7 is shown. The lever controls the flow of the external compressed air supply. In the preferred embodiment, the pinch lever would be fabricated from a thin rigid strip of metal that is bent at two locations to take advantage of mechanical leverage. As shown in the figure, one bend contacts the inner wall of the hollow elongated handle and operates as a pivot point. A second bend is shown which provides the lever with a means to contact the air supply line 6, compress it and inhibit the gaseous medium flow. A passage is provided in the lever located between the first and second bend to prevent contact with the material supply tube 5. A compressed air supply can be found in most environments in which the abrading apparatus will operate however where no supply exists a pressurized air or nitrogen bottle can be provided. In the preferred embodiment an operating pressure of 80 to 100 pounds per square inch should be supplied, however it can be appreciated that the apparatus will operate at a variety of air pressures. Without depressing the pinch lever button 8 the pinch lever 7 acts to prohibit the air stream flow in the compressed air supply line 6. The supply line 6 is envisioned to be compressible or deformable and could be made of a variety of flexible tubing materials. The pinch lever spring 9 contacts the lever button 8 and the tubular housing 11 to draw the forward end of the pinch lever toward the housing wall; as the forward end of the pinch lever is drawn toward the housing wall the rearward end of the lever compresses the external air supply tube 6 against the housing which compresses the air supply line 6 and inhibits the air supply flow. The pinch lever tie down screw 10 secures the pinch lever button 8 to the pinch lever 7. As depicted in both FIGS. 1 & 2, the pinch lever 7 provides a passage for the supply material tube 5 such that the tube 5 will at no time be deformed or compressed. Although the pinch lever control is envisioned to be the best means of controlling the apparatus it can be appreciated that a variety of other control devices such as a foot pedal could serve to control the air flow.

Referring now to FIG. 3 the nozzle body 2 and nozzle tip 1 are shown in detail. The nozzle body 1 provides a means for receiving the nozzle tip 1, the external compressed air supply tube 6 and the pulverulent material supply tube 5. The nozzle body 2 can be composed of a variety of materials; in the preferred embodiment the nozzle body 2 should be manufactured from a soft metal such as aluminum; which can be machined at a low cost, and is lightweight. The forward tip of the nozzle body 2 is hollowed in order to receive the nozzle tip 1. The nozzle tip 1 should be composed of a hard material since the pulverulent material, typically aluminum oxide is abrasive and can quickly erode the aluminum body. In the preferred embodiment a tip manufactured from Tungsten Carbide will provide a long lasting nozzle tip 1. The carbide tip 1 is designed to be received and secured within the nozzle body 2. In the preferred embodiment the nozzle tip 1 may be cemented in place allowing for easy replacement of the tip when it becomes worn beyond operational limits. It can be appreciated that a contra-angle tip can be employed to direct the air and pulverulent material mixture in an off angle direction which can aid the user in directing the jet stream in confined spaces.

Referring again to FIG. 3 a vortex mixing chamber 24 is shown enclosed within the nozzle body 2; said chamber 24 is designed to allow the pulverulent material 17 to mix with and become entrained in the air stream and pass through the nozzle tip 1. During operation, the external air stream continues at a constant velocity through the external air supply line 6 and through the nozzle body 2 and the carbide nozzle tip 1. The moving air stream passing through the vortex chamber 24 generates a vacuum in the pulverulent material supply tube 5; this causes a suction which aspirates material from the supply bottle 16, through the supply tube 5 and pick-up stem 12. Said pick up orifice 14 as shown in figure has a orifice diameter which is smaller in diameter than the diameters of the inner stem 13 and material supply line 5. The smaller orifice diameter is designed to prevent the pulverulent material from clogging within the inner stem 13 or material supply tube 5 by only allowing particles much smaller in diameter that the diameters of the inner stem and material supply tube; thereby decreasing the potential to clogging and blockage. And out into the vortex mixing chamber 24 where the material becomes entrained in the fast moving air stream and is discharged with the air through the carbide nozzle orifice 1.

Now referring to FIG. 4 a pulverulent material pick-up apparatus is shown. The system comprises an inner pick-up stem 13 secured to a supply receiving member 22 through a threaded pick-up stem holder 21; an outer pick-up stem member 12 housing the inner stem and secured to the receiving member 22; and a pick-up orifice 14 secured to one end of the outer pick-up stem 12. Referring again to FIG. 1 a pulverulent supply material reservoir 25 is shown comprising a material supply jar 16 and a jar lid 19 with a center grommet 15 fashioned to receive the outer pick-up stem 12. The outer pick-up stem 12 and grommet 15 are designed such that the grommet 15 and jar lid 19 will receive and secure the outer pickup stem 12 but will allow the user to quickly slide the jar lid on and off the outer pick-up stem 12 with moderate hand pressure applied. The jar lid 19 and outer pick-up stem 12 are provided with vent holes to allow the passage of fresh air into the supply jar 16 and the inner pick-up stem 13. During operation the vent holes allow air external to the system to mix with the pulverulent material 17. Similar to a carburetor system the mixture of outside air and pulverulent material 17 is drawn through the inner supply stem 13 by the vacuum created within the vortex chamber 24.

Referring once again to FIG. 1 the means to backflush and remove any clogs within the solid material supply line 5 in shown. This procedure can be accomplished by placing an object over the carbide tip 1 while quickly depressing the pinch lever button 8 resulting in compressed air to be forced through the solid material supply line 5 in a reverse direction effectively an quickly removing all clogs.

Referring now to FIG. 5 the apparatus is shown in a typical operation. The rear mounted solid material reservoir 25 is clearly shown and the obvious advantage of its location can be inferred. A human right hand is shown holding the apparatus in the correct operating fashion. The right hand thumb is shown controlling the pinch lever button 8. As depicted the apparatus is slim and fits the human hand much like a pen or pencil would. Also depicted is the unobstructed nozzle tip 1 designed for use in confined environments.

We claim:

1. A lightweight, hand held apparatus for abrading, polishing, cleaning, or etching the surface of an object with a stream of fluid containing a mixture of pulverulent material and a gaseous medium, comprising a hollow elongated tube constituting a handle and a nozzle having at least one orifice to discharge the afor stream of fluid against the surface, a vortex mixing chamber for mixing the gaseous medium and pulverulent material, a means of receiving a compressed gas flow and urging the gaseous flow into the vortex mixing chamber, an air and pulverulent material receiving member disposed at one end of the tube for receiving an air supply line and a pulverulent supply line, a pulverulent supply reservoir, and a means to control the flow of the pulverulent material and gaseous medium mixture, wherein the means to control the flow of the pulverulent material and gaseous medium mixture comprises a pinch lever disposed inside the hollow elongated tube, wherein the pinch lever comprises a first portion, substantially parallel to the hollow elongated tube, connected to a pinch lever button at one end and to a second portion at the other end; the second portion is disposed at an angle relative to the first portion and the connection between the first and second portions form a pivot point against the inner wall of the hollow elongated tube; the second portion is connected to a third portion wherein the third portion is disposed at an angle relative to the second portion; the third portion consists of a rounded end portion to pinch the air supply line when the pinch lever button is depressed and a passageway to allow the pulverulent supply line to pass through the third portion to prevent the pulverulent supply line from being pinched.

2. The apparatus of claim 1, wherein the aforementioned pulverulent supply reservoir is located on one end of the hollow elongated tubular housing and the nozzle is located on the opposite end.

3. The apparatus of claim 1, with the addition of a spring located between the pinch liner button and the outer wall of the hollow elongated housing provided such that the lever will be rotated in a manner that the lever will compress the gaseous medium supply tube which spring force however can be mechanical overcome by human force.

4. The apparatus of claim 1, wherein the air and pulverulent material receiving member comprises an outer and inner pick up stem, a pick up orifice fabricated to only allow passage of pulverulent material smaller in diameter than the inner diameter of either the inner pick up stem or the supply material tube, and a threaded interface which connects the inner and outer pick stem to the air and pulverulent material receiving member located at one end of the hollow elongated housing handle.

5. The apparatus of claim 4, wherein the pulverulent material supply reservoir comprises a containment basin and a containment basin closure lid which employs a means to secure the lid to the outer stem through means of a friction fit interface.

6. The apparatus of claim 1, wherein the nozzle on exit tip made of a comprises hardened metal hollow tube and, a receiving member to secure said tube.

7. The invention of claim 1, comprising an improved means to remove all clogs of pulverulent material within the apparatus.

* * * * *